United States Patent [19]
Sotoya et al.

[11] Patent Number: 5,488,168
[45] Date of Patent: Jan. 30, 1996

[54] TERTIARY AMINO ALCOHOL AND METHOD OF PRODUCING THE SAME

[75] Inventors: Kohshiro Sotoya; Hiroshi Abe; Jun Aikawa; Hideki Taniguchi; Uichiro Nishimoto, all of Wakayama, Japan

[73] Assignee: Kao Corporation, Tokyo, Japan

[21] Appl. No.: 46,924

[22] Filed: Apr. 14, 1993

Related U.S. Application Data

[63] Continuation of Ser. No. 563,712, Aug. 7, 1990, abandoned.

[30] Foreign Application Priority Data

Aug. 25, 1989 [JP] Japan .................................. 1-219046

[51] Int. Cl.$^6$ .................................. C07C 215/08
[52] U.S. Cl. .................. 564/506; 564/367; 564/452; 564/504; 564/505
[58] Field of Search .................. 564/367, 452, 564/504, 505, 506

[56] References Cited

U.S. PATENT DOCUMENTS

| | | | |
|---|---|---|---|
| 3,176,040 | 3/1965 | Wilkinson et al. | 564/506 |
| 3,331,892 | 7/1967 | Cyba | 558/186 |
| 3,364,262 | 1/1968 | Cyba | 564/453 |
| 3,369,905 | 2/1968 | Jones | 564/505 |
| 3,371,039 | 2/1968 | Cyba | 252/32.7 E |
| 3,445,422 | 5/1969 | Cyba | 524/185 |
| 3,872,171 | 3/1975 | Cronin et al. | 564/506 |
| 4,034,040 | 7/1977 | Cronin et al. | 564/388 |
| 4,101,690 | 7/1978 | Miyamoto et al. | 564/367 |
| 4,258,061 | 3/1981 | Cronin et al. | 514/667 |
| 4,341,716 | 7/1982 | Diery et al. | 564/506 |
| 4,404,403 | 9/1983 | Swift et al. | 564/473 |
| 4,404,404 | 9/1983 | Swift et al. | 564/473 |
| 4,409,399 | 10/1983 | Swift et al. | 564/473 |
| 4,433,170 | 2/1984 | Zimmerman et al. | 564/506 |
| 4,491,583 | 1/1985 | Cronin et al. | 514/255 |
| 4,684,729 | 8/1987 | Duguette et al. | 544/357 |
| 4,927,931 | 5/1990 | Molzahn | 544/357 |
| 4,970,211 | 11/1990 | Fenyes et al. | 544/357 |
| 5,306,725 | 4/1995 | Harada | 521/78 |

FOREIGN PATENT DOCUMENTS

| | | |
|---|---|---|
| 0384766 | 2/1990 | European Pat. Off. . |
| 0439186A2 | 7/1991 | European Pat. Off. . |
| 0502516A2 | 9/1992 | European Pat. Off. . |
| 1361810 | 4/1964 | France . |
| 2102116 | 7/1972 | France . |
| 1493387 | 8/1965 | Germany . |
| 1492234 | 2/1976 | Hungary . |
| 57-849 | 1/1982 | Japan . |
| 57-55704 | 11/1982 | Japan . |
| 59-12106 | 3/1984 | Japan . |
| 59-14457 | 4/1984 | Japan . |
| 60-1297 | 1/1985 | Japan . |
| 60-48499 | 10/1985 | Japan . |
| 61-60636 | 3/1986 | Japan . |
| 61-37243 | 8/1986 | Japan . |
| 61-37242 | 8/1986 | Japan . |
| 61-278528 | 12/1986 | Japan . |
| 62-51646 | 3/1987 | Japan . |
| 62-28947 | 6/1987 | Japan . |
| 62-31009 | 7/1987 | Japan . |
| 129182 | 6/1989 | Japan . |

OTHER PUBLICATIONS

CA 112:169001, 1989.
El-Merzabani, *Chem Pharm Bull*, 21(7), pp. 1560–1563, 1973.
Pelaprat, *J Med Chem*, 23, pp. 1336–1343, 1980.
Bradshaw, *J Heterocyclic Chem*, 26, pp. 565–569, May 1989.
Krakowiak et al., *J. Heterocycl. Chem*. 26(3), 661–665 (1989).
Adrian et al., Bulletin de la Societe Chimique de France 1971, No. 2, p. 638.
Houben–Weyl, Methoden der Organischen Chemie, p. 133 (1957).
M. I. Dorokhova et al, Chemical Abstracts, vol. 85, No. 11, Sep. 13, 1976, p. 541.
G. Faust et al, Chemical Abstracts, vol. 59, No. 13, Dec. 23, 1963, col. 15157.
G. Adrian et al, Bulletin De La Societe Chimique De France, No. 2, 1971, pp. 638–642.

*Primary Examiner*—C. Warren Ivy
*Assistant Examiner*—D. Margaret M. Mach
*Attorney, Agent, or Firm*—Birch, Stewart, Kolasch & Birch

[57] ABSTRACT

A tertiary amino alcohol, being useful as an emulsifier, is defined by the formula (1) or (2):

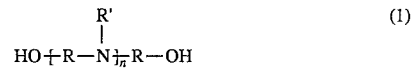

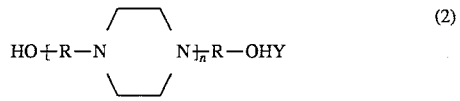

where R is a $C_2$ to $C_{24}$ straight-chain or branched alkylene group, an alicyclic alkylene group, an aralkylene group or $-(CH_2CH_2O)_p-(CH_2CH_2)_q-$ (where p is 0 or a positive integer and q is a positive integer), R' is a $C_1$ to $C_{24}$ straight-chain or branched alkyl group or an aralkyl group and n is a positive integer of 2 to 50.

2 Claims, 2 Drawing Sheets

TERTIARY AMINO ALCOHOL AND METHOD OF PRODUCING THE SAME

This application is a continuation, of application Ser. No. 07/563,712 filed on Aug. 7, 1990, now abandoned.

The present invention provides a novel tertiary amino alcohol. The tertiary amino alcohol itself can be used as an emulsifier, an epoxy curing agent, a urethane catalyst, a flotation reagent, an extractant, a lubricant additive, and the like, and various derivatives can be made from the alcohol, such as, quaternary ammonium salts, benzalkonium salts, carbobetaine, amine oxides, etc. Furthermore, because the tertiary amino alcohol possesses a terminal alcohol group various modifications can be made using procedures such as esterification, sulfation, phosphation, amination, halogenation, and so forth.

Prior Art

The tertiary amino alcohol of the present invention which has a tertiary amino group in its main chain and a method of producing such an alcohol are not found in any of known publications.

For instance, a method of producing a polyamine having a terminal amino group by the reaction between a diol and $NH_3$ is disclosed in Japanese Patent Laid-Open No. 278528/1986 (Texaco) and Japanese Patent Laid-Open No. 51646/1987 (W. R. Grace & Co.) and a method of producing a tertiary amine by the condensation reaction between a di-secondary amine and diaryl iodide is disclosed in Japanese Patent Publication No. 29182/1990 (Xerox Corporation), etc. A method of producing a polyalkylenepolyamine by the polycondensation of a lower diamine and hexamethylenediamine is disclosed in Japanese Patent Publication No. 31009/1987 (Nippon Sekiyu), and so forth. A method of obtaining a polycation by the reaction between a di-tertiary amine and a dihalide, as a polyamide derivative, is disclosed in Japanese Patent Publication Nos. 37242/1986 and 37243/1986 (Loreal).

However, the tertiary amino alcohol which incorporates a tertiary amino group into the skeleton and, whose terminal is a hydroxyl group as well as its method of production are entirely novel.

As described above, an amino alcohol having a tertiary amino group in its main chain skeleton and a method of its production are not disclosed in the prior art. By production of the a tertiary amino alcohol, the development of applications different from those of conventional amines and amine derivatives is made possible. Where those peculiar features cannot be obtained by monomers, will be brought forth by oligomerizing or polymerizing the amine. Thus, the development of novel fields of application of the amines is expected.

SUMMARY OF THE INVENTION

In view of the circumstances described above, the inventors of the present invention have conducted extensive studies and have completed the present invention.

Namely, the present invention provides a tertiary amino alcohol represented by the general formula (1) or (2):

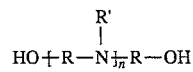

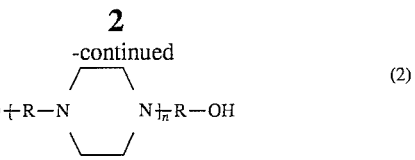

where R is a $C_2$ to $C_{24}$ straight-chain or branched alkylene group, an alicyclic alkylene group, an aralkylene group or $-(CH_2CH_2O)_p-)CH_2CH_2-(_q$ p is 0 or a positive integer and q i a positive integer), R' is a $C_1$ to $C_{24}$ straightchain or branched alkyl group or an aralkyl group and n is a positive integer of 2 to 50.

The present invention also provides a method of producing the tertiary amine described above by using a copper—fourth period transition metal element—Group VIII platinum group element catalyst which may contain an alkali metal or alkaline earth metal, for producing the tertiary amino alcohol by reacting a diol or a dialdehyde with a primary amine or piperazine. The diol or dialdehyde to be used in the present invention is a $C_2$ to $C_{24}$ straight-chain or branched diol or dialdehyde. Particular examples thereof include 1,3-butanediol, 1,4-butanediol, 1,5-pentanediol, 1,6-hexanediol, 1,9-nonanediol, 1,10-decanediol, diethylene glycol, triethylene glycol, tetramethylene glycol, 1,4-cyclohexanedimethanol, bis phenol A/ethylene oxide adduct, and their corresponding aldehydes.

The primary amine to be used in the present invention is a straight-chain or branched $C_1$ to $C_{24}$ primary amine or an aromatic amine. Particular examples thereof include methylamine, propylamine, isopropylamine, butylamine, 2-ethylhexylamine, heptylamine, octylamine, decylamine, dodecylamine, cetylamine, stearylamine, docosylamine, oleylamine, benzylamine, and phenethylamine.

The present invention provides a novel tertiary amino alcohol which has a tertiary amino group at its main chain and hydroxyl groups at both terminals and also a method of producing such a tertiary amino alcohol by reacting the diol or dialdehyde with the primary amine or piperazine to effect tertiary amination.

The tertiary amination technique is disclosed in Japanese Patent Publication No. 849/1982 and No. 12106/1984, Japanese Patent Laid-Open No. 55704/1982, Japanese Patent Publication No. 1297/1985 (Hoechst) and No. 48499/1985 (Shell), U.S. Pat. Nos. 4,404,403, 4,404,404 and 4,409,399 (Onyx), Japanese Patent Laid-Open No. 60636/1986 (Shering) and No. 14457/1984 (Texaco), Japanese Patent Publication No. 28947/1987 (Shin-Nippon Rika), and the like. However, these methods are not entirely satisfactory, because the catalysts disclosed in these references do not provide sufficient reactivity and the intended product cannot be obtained in sufficient yield.

In contrast, the catalyst used in the present invention is a copper—fourth period transition metal element—Group VIII platinum group element catalyst which may contain an alkali metal or alkaline earth metal, and the intended tertiary amino alcohol can be obtained in sufficient yield by the method which uses such a catalyst for the first time.

The fourth period transition metal element constituting the copper—fourth period transition metal element—Group VIII platinum group element catalyst is at least one member selected from the group consisting of chromium, manganese, iron, cobalt, nickel and zinc and the Group VIII platinum group element is at least one member selected from the group consisting of platinum, palladium, ruthenium and rhodium. The molar ratio of the copper of the copper—fourth period transition metal element—Group VIII platinum group element catalyst to the metal atom of the fourth period transition metal element is 1:9 to 9:1 in terms of a copper to fourth period transition metal ratio, and the molar ratio of the Group VIII platinum group element to the sum of the copper and the fourth period transition metal element is 0.001 to 0.1.

In the metal composition of the catalyst used in the present invention, copper, the fourth period transition metal element and the platinum group element are essential, though the catalyst may further contain an alkali metal or alkaline earth metal. Therefore, the catalyst suitable for the present invention can be in various forms.

In other words in the present invention, the effect due to the interaction among the three components of copper, the fourth period transition metal element and the Group VIII platinum group element or the four components including the alkali metal or alkaline earth metal (hereinafter referred to as the "fourth component") in addition to the former three can be exhibited only when the three or four components exist as the catalyst composition inside the reaction system.

In the catalyst used in the present invention, the composition of the three or four components described above has the essential catalytic function and, when a diol or dialdehyde is reacted with an amine, the catalytic activity can be exhibited only by the reduction of each metal component in the hydrogen atmosphere. Accordingly, the present invention is not limited to a difference in the forms of the metals before the reduction and the state inside the system after the reduction, and the form may be such that an interaction is exhibited among the copper, the fourth period transition metal element and the Group VIII platinum group element or among these three and the fourth component due to the reduction in a hydrogen atmosphere.

Accordingly, the form of the metal suitable for the catalyst used in the production method of the present invention may be any one of the following:

(1) a form which allows the copper, the fourth period transition metal element and the Group VIII platinum group element or these three components and the metal of the fourth component or its oxide or hydroxide or their mixture to be dispersed in the reaction medium;

(2) a form which allows the three components of the copper, the fourth period transition metal element and the Group VIII platinum group element or the four components inclusive of the fourth component to be supported on the same suitable support and dispersed in the reaction medium;

(3) a form wherein a salt of an aliphatic carboxylic acid with the three components of the copper, the fourth period transition metal element and the Group VIII platinum group metal or a salt of the acid with the four components inclusive of the fourth component can form a metal or a complex thereof stabilized by a suitable ligand colloid to thereby give a homogenous system in the reaction medium; and (4) a mixture of metals having the form which allows dispersion in the reaction medium such as forms (1) to (2) with metals having the form which gives a homogeneous system in the reaction medium such as form (3), or a form which allows dispersion before hydrogen reduction and gives a homogeneous system after hydrogen reduction.

In brief, it will suffice when the metals of the three or four components as the essential components of the catalyst used in the present invention interact among one another by the operation in a hydrogen atmosphere.

A further preferred form of the catalyst used in the present invention is where the component metals described above are uniformly supported on a suitable support thereby providing stabilization of the catalytic metals, and thus the fixation of the active surface and the resistance against catalyst poison.

When the three-component metals of copper fourth period transition metal element—Group VIII platinum group element or the four-component metals inclusive of the fourth component are to be supported on the support, ordinary catalyst supports, such as alumina, silica/alumina, diatomaceous earth, silica, active carbon, natural and synthetic zeolites, and the like, can be used. Though the quantity of the catalyst to be supported can be determined arbitrarily, it may range generally from 5 to 70 wt % based on the support.

Various methods can be selected as the method of supporting the three- or four-component metals on the support surface. In this case, oxides and hydroxides of copper, fourth period transition metal element, Group VIII platinum group element and fourth component or various metal salts thereof can be used as the starting materials of the catalyst. The metal salts include, for example, chlorides, sulfates, nitrates, acetates, and aliphatic carboxylates of copper, fourth period transition metal element, Group VIII platinum group element and the fourth component. It is further possible to use their metal complexes, such as acetylacetone complexes of copper, fourth period transition metal element and Group VIII platinum group element and carbonyl complexes, amine complexes and phosphine complexes of the Group VIII platinum group element.

When the catalyst is prepared by supporting these metals on the support, the following various methods can be employed. For example, it is possible to employ a method which comprises dipping the support in a solution of suitable salts of copper, fourth period transition metal element, Group VIII platinum group element and fourth component and drying and sintering the support after sufficient impregnation (impregnation method). It is also possible to employ a method which comprises mixing sufficiently the support and an aqueous solution of suitable salts of copper, fourth period transition metal element and Group VIII platinum group element, adding an aqueous solution of an alkali such as sodium carbonate, sodium hydroxide or aqueous ammonia so as to precipitate the metal salts on the support, or mixing sufficiently an aqueous solution of suitable salts of copper, fourth period transition metal element and Group VIII platinum group element with an aqueous slurry of the support, adding simultaneously an aqueous solution of an alkali such as sodium carbonate, sodium hydroxide or aqueous ammonia so that the pH of the slurry becomes constant (e.g. a pH of 7), precipitating the metal salts on the support, drying and sintering the support so as to prepare a copper—fourth period transition metal element—Group VIII platinum group element catalyst, putting the resulting three-component system catalyst into an aqueous solution of an alkali metal salt or alkaline earth metal when the four-component catalyst is to be obtained, and drying and sintering the support after sufficient impregnation (a combination of coprecipitation and impregnation). Another method that can be used is a method which effects ion-exchange with hydrogen or metal contained in zeolite (ion exchange method). In short, any of known methods may be used. In the case of the coprecipitation method, sufficiently washing with water is conducted after the precipitation of the metals, and drying is conducted near 100° C. with the sintering then being conducted at 300° to 700° C. to obtain the catalyst.

Another effective method comprises supporting only copper or only copper and the fourth period transition metal element on the support by any of the above methods, adding the Group VIII platinum group element, the fourth component, the aliphatic carboxylate or the complex before the reaction, and forming a complex of the copper, the fourth period transition metal element, the Group VIII platinum group element and the fourth component in the reaction medium in a hydrogen atmosphere.

The catalysts obtained by the various methods described above may have preferably a form in which the three or four components are uniformly supported on the same support.

In the catalyst used in the present invention, the three components of copper, the fourth period transition metal element and the Group VIII platinum group element are essentially indispensable.

The method of producing the tertiary amino alcohol in accordance with the present invention will now be described in further detail.

A tertiary amino alcohol can be produced by reacting a diol or dialdehyde with a primary amine or piperazie according to the method of the present invention which comprises using a catalyst having a composition consisting of copper—nickel—Group VIII platinum group element, copper—chromium— Group VIII platinum group element, copper—zinc—Group VIII platinum group element, copper—manganese—Group VIII platinum group element, copper—iron—Group VIII platinum group element, copper—cobalt—Group VIII platinum group element, or the like, and these catalysts further containing the fourth component, and carrying out the reaction under an atmospheric or elevated pressure at 150° to 250° C. while discharging either continuously or intermittently water generated by the reaction in the presence of these catalysts.

In this reaction, the diol or dialdehyde may be added continuously during the reaction or may be fed at the beginning. Alternatively, a predetermined amount thereof may be fed in several portions.

When the primary amine is gas, it is fed either continuously or intermittently during the reaction or a predetermined quantity thereof may be fed at once under an elevated pressure. When the primary amine is liquid, it is fed continuously or a predetermined quantity thereof may be fed at the beginning.

The molar ratio of the amine to the diol or dialdehyde must be at least 0.7, preferably 1.0, and in the case of a gaseous amine, the gas which is fed in excessive amounts together with hydrogen may be recovered and reused by recycling.

In the method of the present invention, the water generated by the reaction between the diol or dialdehyde and the primary amine or piperazine is preferably withdrawn outside the reaction system. When the water is not taken out of the system, the catalytic activity and selectivity in many cases drops. If the reaction is carried out without removing the water, for example, disproportionation products of the amine are formed in large quantity or large quantities of aldehyde condensates are formed, so that the yield of the intended tertiary amino alcohol drops.

The formed water may be removed either intermittently or continuously during the reaction, and it will suffice when the water is removed suitably without remaining for a long time in the reaction system. It is, however, preferred to continuously remove the water each time when it is formed. More specifically, it is general practice to introduce a suitable quantity of a hydrogen gas into the reaction system during the reaction and to distill the formed water together with the hydrogen gas. The hydrogen gas can be recycled for use by condensing and separating the water in a condenser. It is also possible to distill azeotropically by adding a suitable solvent to the reaction system or to add an inert solvent so as to reduce the viscosity of the product.

In the present invention, although the catalyst may be reduced in advance separately by the hydrogen gas, the catalyst can also be reduced when the catalyst is put into the reactor together with the diol or dialdehyde as the starting materials and heating the reaction mixture to a reaction temperature while introducing a hydrogen gas or, when the amine is gas, a mixture of a hydrogen gas with the gaseous amine.

The embodiment for practising the method of the present invention will now be described briefly.

When hydrogen and a gaseous amine are used, a diol or dialdehyde as the starting material and a catalyst are fed to a reactor equipped with a tube for introducing the amine and a condenser and a separator for condensing and separating water generated by the reaction, an excess amount of amine and an evaporating oily substance. Though an arbitrary amount of the catalyst may be used, the amount is generally from 1 to 10 wt % on the basis of the diol or dialdehyde fed.

After the reaction system is purged with a nitrogen gas, the elevation of temperature is started while introducing hydrogen alone or together with a small amount of a gaseous amine. When a liquid amine is used, the amine is fed at once after the temperature reaches a predetermined temperature, or dropped into the reaction system in small portions.

The reaction temperature is generally from about 150° to about 250° C., though the temperature outside this range can be employed depending on the kind of the starting materials. The catalyst is reduced during this temperature rise into a catalyst in an activated state. After the temperature reaches a predetermined temperature, the reaction is started by introducing e.g. dropping the amine in.

During the reaction, the formed water is discharged outside the system together with gaseous matters (hydrogen and excessive gaseous amine) and a small amount of oily substances, and is then separated from the oily substances through the condenser and the separator. The oily substances thus separated are returned to the reactor. As a result of analysis of the gaseous matters (excessive hydrogen and gaseous amine), it is found that they scarcely contain any by-products (e.g. hydrocarbons), so that they can be reused by use of a circulator without any special refining step.

After the reaction is completed, the catalyst is filtered off by a suitable method to obtain the product.

EXAMPLE

Now the present invention will be described in further detail with some examples thereof, though the invention is not particularly limited thereto.

Preparation of the catalyst

A ternary copper—fourth period transition metal element—Group VIII platinum group element catalyst supported on synthetic zeolite was prepared in the following way.

Synthetic zeolite was fed into a 1-l flask and then a solution prepared by dissolving copper nitrate, nickel nitrate and palladium chloride in water so as to attain a molar ratio in terms of the metal atom of Cu:Ni:Pd of 4:1:0.1 was added thereto. The mixture was heated with stirring. A 10% aqueous $Na_2CO_3$ solution was gradually added dropwise at 90°

C. After aging for one hour, the precipitate was filtered, washed with water, dried at 80° C. for 10 hours and then sintered at 400° C. for three hours. The quantity of the supported metal oxide was 50% based on the support.

A catalyst having a molar ratio of Cu:Zn:Rh of 4:1:0.1 was prepared similarly.

Furthermore a catalyst having a molar ratio of Cu:Ni:Ru of 4:1:0.01 was prepared similarly, the resulting ternary catalyst was immersed sufficiently in an aqueous lithium carbonate solution (molar ratio: Ni:Li of 1:0.05), dried again at 80° C. for ten hours and sintered at 300° C. for one hour to obtain a quaternary catalyst of Cu/Ni/Ru/Li. The quantity of the supported catalyst was 50% in the same way as above.

The catalysts thus prepared were used in the following Examples.

Example 1

A reaction between 1,6-hexanediol and monomethylamine was carried out.

600 g of 1,6-hexanediol and 2.4 g (4 wt % on the basis of the starting diol) of the catalyst described above (Cu/Ni/Pd catalyst having a molar ratio of 4/1/0.1; hereinafter, this catalyst will be used throughout all the Examples other than Examples 7 and 9) were fed into a 1-l flask equipped with a condenser and a separator for separating the formed water, and the reaction system was purged with nitrogen under stirring. Then the temperature elevation was started. When the temperature inside the system reached 100° C., a hydrogen gas was blown into the system at a rate of 10 l/hr by use of a flow meter and the temperature was raised to 180° C. A mixture of monomethylamine and hydrogen gas was blown into the reaction system at a flow rate of 40 l/hr at this temperature and the reaction was traced by an amine value and a hydroxyl value. The reaction was carried out for about four hours. After the reaction, the catalyst was filtered away to obtain a pale brown viscous liquid.

The product was subjected to various analyses.

First of all, as a result of mass spectroscopic analysis, it was confirmed from the molecular weight that the tertiary amino alcohols represented by the following formula wherein n is 1 to 8 were formed:

$$HO+C_6H_{12}-N\!\!\!\!+_{\!\!n}C_6H_{12}-OH$$
$$|$$
$$CH_3$$

Figure 1:
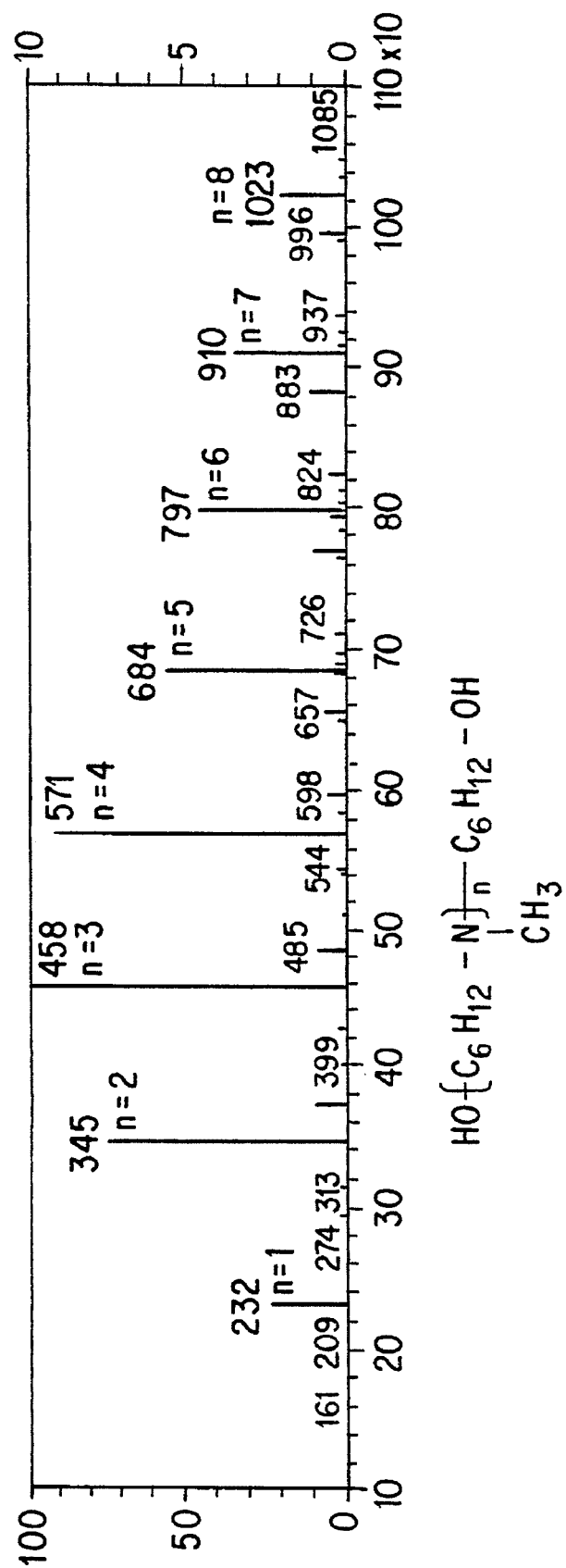
FIG. 1 is a diagram showing the mass spectrum of the tertiary amino alcohol obtained in Example 1.

FIG. 1 shows the mass spectrum of this compound.

Figure 2:
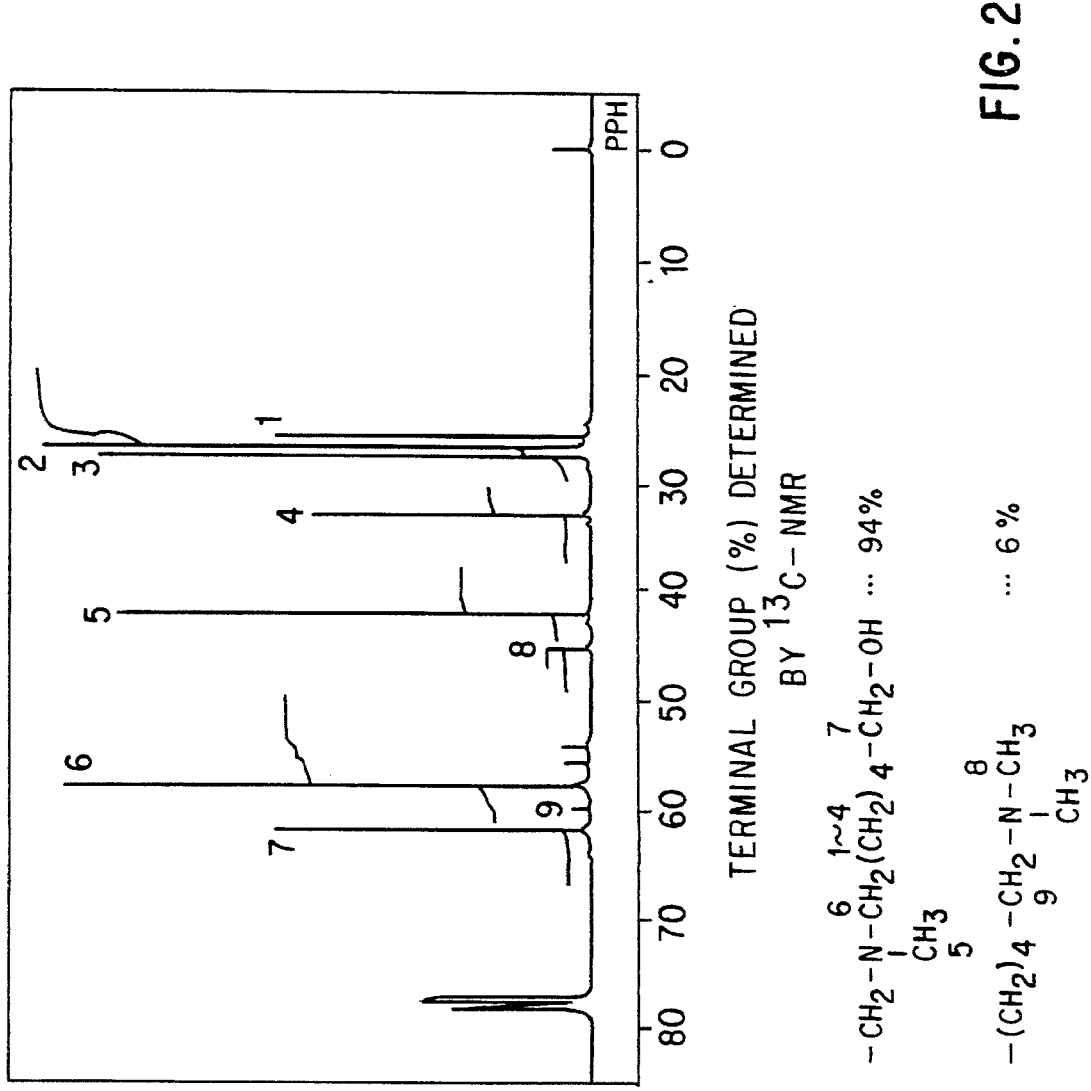
FIG. 2 is a diagram showing its $^{13}C$ NMR spectrum.

Next, a $^{13}$C NMR spectrum was measured with a 270 MHz NMR (JMR-GX270WB) in order to prove that the terminal was alcoholic. According to the calculation from the area ratio, 94% of the terminal groups were alcoholic [the following formula (1)] while 6% thereof were dimethylamino groups [the following formula (2)] (formed by the reaction with dimethylamine resulting from the disproportionation of monomethylamine). FIG. 2 shows the $^{13}$C NMR spectrum.

① 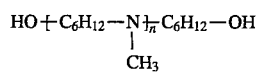 94 mol %

② 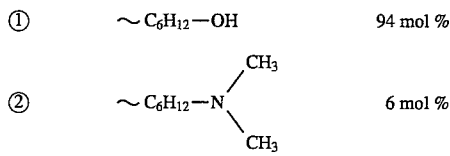 6 mol %

Further, according to the VPO, the molecular weight was 425 ($\bar{n}$=2.7) and, according to the calculation value based on the $^{13}$C NMR spectrum, $\bar{n}$ was approximately 2.4, which was in good agreement with the observed value. As to the observed values of the amine values, the total amine value was 355.7 and the tertiary amine value was 353.7, which was in good agreement with the theoretical value 355 when $\bar{n}$ was 2.7. It was thus confirmed that the amino alcohol of the present invention having the tertiary amino group at its main chain could be obtained.

Example 2

The reaction was carried out for about 15 hours under the same conditions as those of Example 1 except that the reaction temperature was 200° C. and the amount of the catalyst was 2 wt % (based on the diol; the same applies in the following Examples), and a tertiary amino alcohol having a molecular weight of 2170 ($\bar{n}$=18.2) according to the VPO and having the same structure as that of Example 1 was obtained.

Example 3

The reaction was carried out for about eight hours under the same conditions as those of Example 1 except that the reaction temperature was 210° C., 1,9-nonanediol was used as the alcohol and the quantity of the catalyst was 2 wt %.

The reaction product was a compound represented by the following formula, and had a molecular weight of 2820 ($\bar{n}$=17.2) according to the VPO:

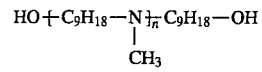

Example 4

The reaction was carried out for about 20 hours at 220° C. with triethylene glycol as the alcohol and the quantity of the catalyst was 4 wt %.

The reaction product was a compound represented by the following formula and had a molecular weight of 1130 ($\bar{n}$=6.8) according to the VPO:

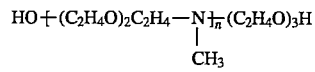

Example 5

1,6-Hexanediol was used as the alcohol and n-butylamine was used as the amine. The quantity of catalyst was 4% and an equimolar amine was added to the diol dropwise in the course of about 30 hours during the reaction, and the reaction was carried out for about 40 hours at 185° C.

The reaction product was a compound represented by the following formula and had a molecular weight of 1530 ($\bar{n}$=9.1) according to the VPO:

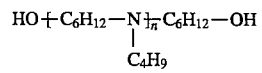

Example 6

1,6-Hexanediol was used as the alcohol and benzylamine was used as the amine. The quantity of catalyst was 4% and an equimolar amine was added to the diol dropwise in the course of about 30 hours during the reaction in the same way as that of Example 5. The reaction was carried out at 180° C. for about 30 hours.

The reaction product was a compound represented by the following formula and had a molecular weight off 666 ($\bar{n}$=2.9) according to the VPO:

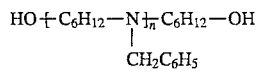

Example 7

1,6-Hexanediol was used as the alcohol and stearylamine was used as the amine. 8% of the catalyst prepared above, that is, the Cu/Zn/Rh catalyst (molar ratio: 4/1/0.1) was used. In the same way as that of Example 5, an equimolar amine was added to the diol dropwise in the course of about 30 hours during the reaction. The reaction was carried out at 200° C. for about 40 hours.

The reaction product was a compound represented by the following formula and had a molecular weight of 1390 ($\bar{n}$=3.4) according to the VPO:

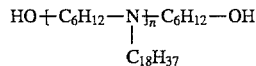

Example 8

1,4-Cyclohexanedimethanol was used as the alcohol and monomethylamine was used as the amine. 2% of the Cu/Ni/Pd catalyst was used as the catalyst with the rest being the same as those of Example 1.

The reaction was carried out at 210° C. for 23 hours,

The reaction product was a compound represented by the following formula and had a molecular weight of 535 ($\bar{n}$=2.8) according to the VPO:

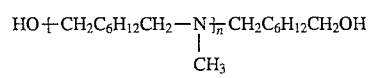

Example 9

Polytetramethylene glycol (PTMG: $\overline{Mw}$=650) was used as the alcohol and monomethylamine was used as the amine, 2% of the. Cu/Ni/Li catalyst prepared above was used as the catalyst with the rest being the same as those of Example 1, The reaction was carried out at 210° C. for 18 hours, The reaction product was a compound represented by the following formula and had a molecular weight of 2050 ($\bar{n}$=2,1) according to the VPO:

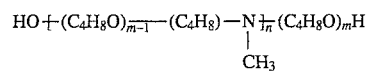

wherein m was 8.8 on an average.

Example 10

1,9-Nonanediol was used as the alcohol and an equimolar piperazine was used as the amine. 4% of the Cu/Ni/Pd catalyst prepared above was used as the catalyst. The reaction was carried out at 200° C. for about 15 hours under an elevated pressure of hydrogen of 10 kg/cm²G.

The reaction product was a compound represented by the following formula and had a molecular weight of 650 ($\bar{n}$=2.3) according to the VPO:

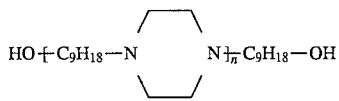

The starting alcohols and amines, the reaction conditions, the molecular weights of the reaction products, $\bar{n}$, and the like in the above Examples 1 to 10 are tabulated in Table 1.

TABLE 1

| | Example No. | | | | | | | | | |
|---|---|---|---|---|---|---|---|---|---|---|
| | 1 | 2 | 3 | 4 | 5 | 6 | 7 | 8 | 9 | 10 |
| starting material | | | | | | | | | | |
| diol | 1,6-HD*2 | 1,6-HD | 1,9-ND*4 | TEG*5 | 1,6-HD | 1,6-HD | 1,6-HD | 1,4-CHDM*6 | PTMG 650*7 | 1,9-ND |
| amine | MMA*3 | MMA | MMA | MMA | n-butylamine | benzylamine | stearylamine | MMA | MMA | piperazine |
| reaction condition | | | | | | | | | | |
| catalyst | Cu/Ni/Pd | → | → | → | → | → | Cu/Zn/Rh | Cu/Ni/Pd | Cu/Ni/Ru/Li | Cu/Ni/Pd |
| catalyst amount (%) | 4 | 2 | 2 | 4 | 4 | 4 | 8 | 2 | 2 | 4 |
| reaction temperature (°C.) | 180 | 200 | 210 | 220 | 185 | 180 | 200 | 210 | 210 | 200 |
| reaction time (hr) | 4 | 15 | 8 | 20 | 41 | 30 | 40 | 23 | 18 | 15 |
| product | | | | | | | | | | |
| —R— | —C$_6$H$_{12}$— | —C$_6$H$_{12}$— | —C$_9$H$_{18}$— | —(C$_2$H$_4$O)$_2$(C$_2$H$_4$)— | —C$_6$H$_{12}$— | —C$_6$H$_{12}$— | —C$_6$H$_{12}$— | —CH$_2$—C$_6$H$_{10}$—CH$_2$— | —(C$_4$H$_8$O)$_{m-1}$—(C$_4$H$_8$)— Mw = 650, m ≈ 8.8 | —C$_9$H$_{18}$— |
| R'— | CH$_3$— | CH$_3$— | CH$_3$— | CH$_3$— | C$_4$H$_9$— | C$_6$H$_5$CH$_2$— | C$_{18}$H$_{37}$— | CH$_3$— | CH$_3$— | piperazine ring |
| molecular weight | 425 | 2170 | 2820 | 1130 | 1530 | 666 | 1390 | 535 | 2050 | 650 |
| n | 2.7 | 18.2 | 17.2 | 6.8 | 9.1 | 2.9 | 3.4 | 2.8 | 2.1 | 2.3 |

Note:
*1 wt %, based on diol
*2 1,6-HD: 1,6-hexanediol
*3 MMA: monomethylamine
*4 1,9-ND: 1,9-nonanediol
*5 TEG: triethylene glycol
*6 1,4-CHDM: 1,4-cyclohexanedimethanol
*7 PTMG650: polytetramethylene glycol

We claim:
1. A tertiary amino alcohol of the formula
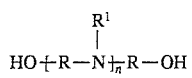
wherein R is a $C_6$–$C_9$ alkylene chain; $R^1$ is methyl, and $\bar{n}$ j.s from 2.7 to 18.2.
2. The tertiary amino alcohol of claim 1, wherein R is hexyl, $R^1$ is methyl and n is 2.7 to 18.2
* * * * *